(12) United States Patent
Wang et al.

(10) Patent No.: US 11,071,549 B2
(45) Date of Patent: Jul. 27, 2021

(54) CIRCULAR STAPLING DEVICE WITH ALIGNMENT SPLINES

(71) Applicant: Covidien LP, Mansfield, MA (US)

(72) Inventors: Zhaokai Wang, Shanghai (CN); Xiliang Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 63 days.

(21) Appl. No.: 16/491,392

(22) PCT Filed: Mar. 23, 2017

(86) PCT No.: PCT/CN2017/077862
§ 371 (c)(1),
(2) Date: Sep. 5, 2019

(87) PCT Pub. No.: WO2018/170831
PCT Pub. Date: Sep. 27, 2018

(65) Prior Publication Data
US 2020/0029970 A1    Jan. 30, 2020

(51) Int. Cl.
*A61B 17/115*    (2006.01)
*A61B 17/072*    (2006.01)

(52) U.S. Cl.
CPC . *A61B 17/1155* (2013.01); *A61B 2017/07264* (2013.01); *A61B 2017/07271* (2013.01)

(58) Field of Classification Search
CPC .............. A61B 17/115; A61B 17/1144; A61B 17/1155; A61B 2017/07257; A61B 2017/00473; A61B 1/31; A61B 17/068
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Partial European Search Report dated Nov. 10, 2020, issued in corresponding EP Appln. No. 17902033, 13 pages.

(Continued)

*Primary Examiner* — Andrew M Tecco
*Assistant Examiner* — Eyamindae C Jallow

(57) ABSTRACT

A surgical stapling device includes an anvil assembly including an anvil shaft and an anvil head assembly that is supported on a distal end portion of the anvil shaft. The anvil shaft defines a longitudinal axis and supports a first spline, a second spline, and a third spline. Each of the first, second, and third splines includes a pair of tapered camming surfaces that meet at a proximal end of the respective spline to define an apex. The apex of the first spline is positioned on the anvil shaft at a location proximal of the apex of the second spline, and the apex of the second spline is positioned on the anvil shaft at a location proximal of the apex of the third spline. In embodiments, each of the splines includes an apex. The apex of the first spline is aligned with a longitudinal axis of the first spline and the apex of the second and third splines are aligned with a longitudinal axis of the second and third splines, respectively.

19 Claims, 7 Drawing Sheets

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |

(56) References Cited

U.S. PATENT DOCUMENTS

| | | |
|---|---|---|
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck |
| 6,676,671 B2 | 1/2004 | Robertson et al. |
| 6,681,979 B2 | 1/2004 | Whitman |
| 6,685,079 B2 | 2/2004 | Sharma |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |

(56) References Cited

U.S. PATENT DOCUMENTS

| | | | |
|---|---|---|---|
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,010,605 B2 * | 4/2015 | Olson ............... A61B 17/1155 227/175.1 |
| 9,301,763 B2 * | 4/2016 | Qiao ..................... A61B 17/115 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0230170 A1 * | 9/2009 | Milliman ........... A61B 17/0684 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0211544 A1 * | 8/2012 | Olson ............... A61B 17/07207 227/176.1 |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |

(56) References Cited

U.S. PATENT DOCUMENTS

| | | |
|---|---|---|
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0367444 A1* | 12/2014 | Williams .......... A61B 17/07207 227/175.1 |
| 2015/0069108 A1* | 3/2015 | Williams ............ A61B 17/1155 227/175.1 |
| 2015/0129636 A1* | 5/2015 | Mulreed .............. A61B 17/115 227/177.1 |
| 2015/0305742 A1* | 10/2015 | Williams ............ A61B 17/1155 227/177.1 |
| 2015/0366562 A1* | 12/2015 | Williams ............ A61B 17/1155 227/175.1 |
| 2016/0143641 A1 | 5/2016 | Sapienza et al. |
| 2016/0157855 A1* | 6/2016 | Williams ............ A61B 17/1155 227/180.1 |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0000475 A1* | 1/2017 | Sgroi, Jr. ........... A61B 17/1155 |
| 2017/0020527 A1* | 1/2017 | Williams ............ A61B 17/1155 |
| 2017/0360443 A1* | 12/2017 | Williams ............ A61B 17/1155 |
| 2018/0242973 A1 | 8/2018 | Guerrera et al. |
| 2018/0242974 A1 | 8/2018 | Guerrera et al. |
| 2019/0059901 A1* | 2/2019 | Guerrera .......... A61B 17/00234 |
| 2019/0290284 A1 | 9/2019 | Guerrera et al. |

FOREIGN PATENT DOCUMENTS

| | | |
|---|---|---|
| CN | 204169888 U | 2/2015 |
| CN | 104905837 A | 9/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 03030745 A1 | 4/2003 |
| WO | 2008107918 A1 | 9/2008 |

OTHER PUBLICATIONS

European Search Report dated Feb. 10, 2021, issued in corresponding EP Appln. No. 17902033, 11 pages.

* cited by examiner

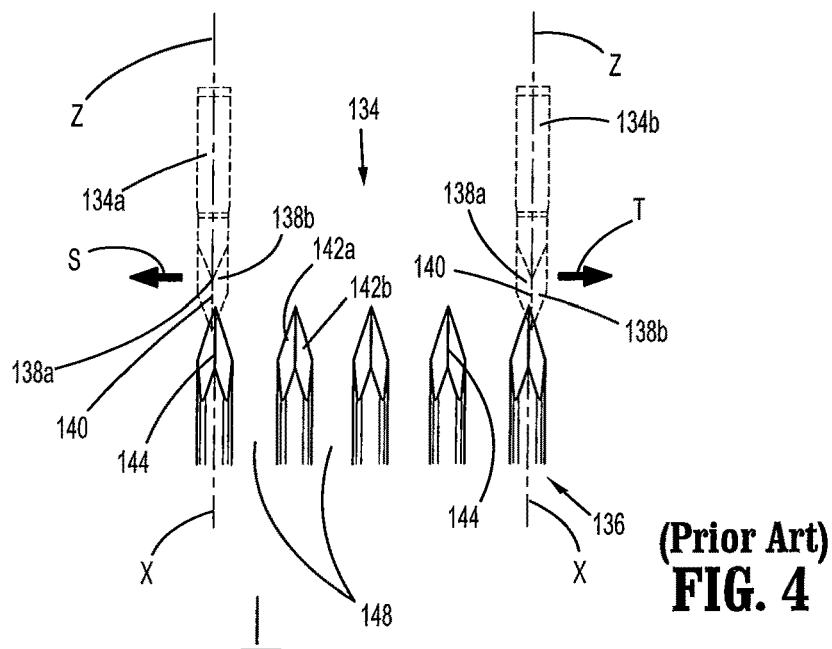
(Prior Art)
FIG. 4
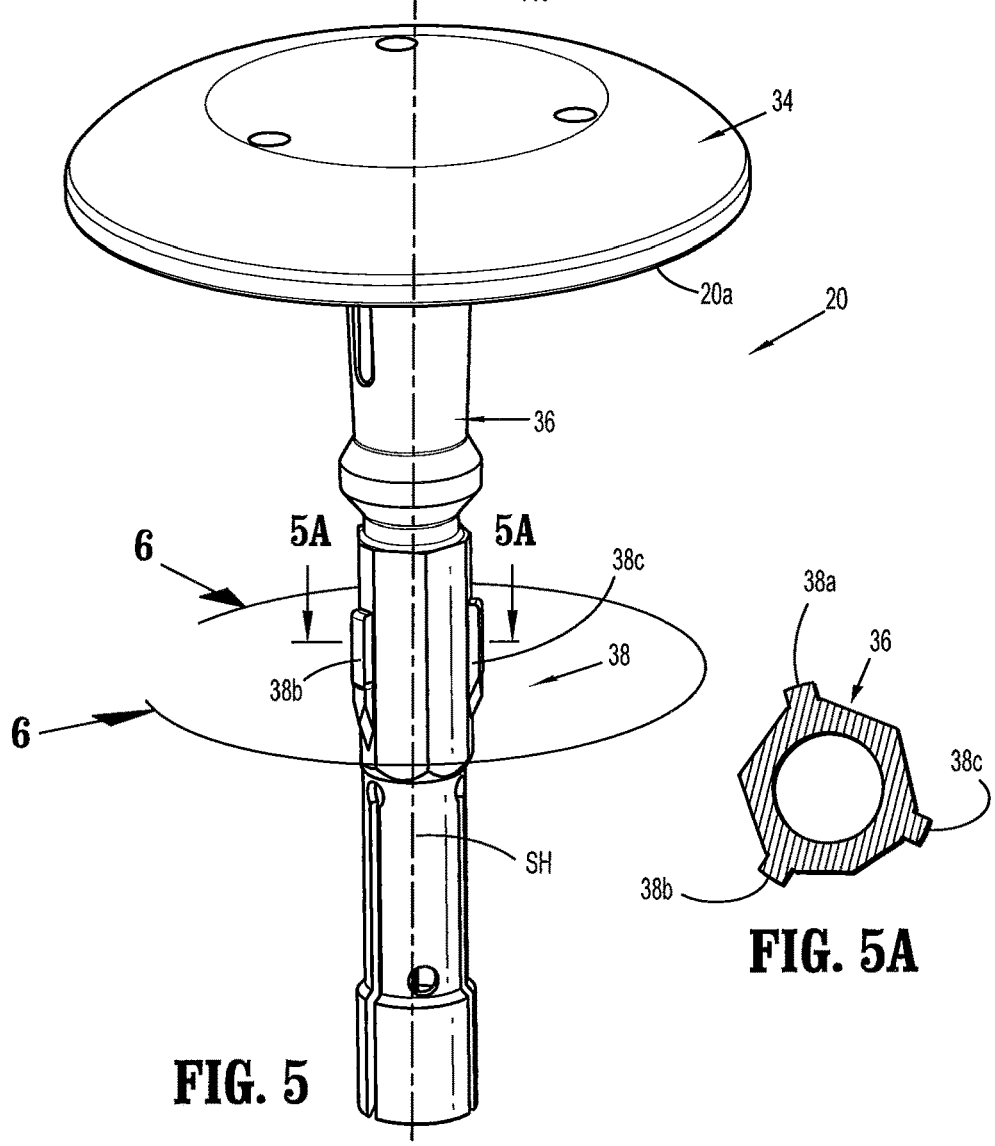
FIG. 5
FIG. 5A

CIRCULAR STAPLING DEVICE WITH ALIGNMENT SPLINES

CROSS-REFERENCE TO RELATED APPLICATIONS

This application is a U.S. National Stage Application filed under 35 U.S.C. § 371(a) which claims the benefit of and priority to International Patent Application Serial No. PCT/CN2017/077862, filed Mar. 23, 2017, the entire disclosure of which is incorporated by reference herein.

BACKGROUND

1. Technical Field

The present disclosure is directed to circular stapling devices, and more particularly, to circular stapling devices including structure to properly align an anvil assembly with a staple cartridge of a shell assembly of the circular stapling device.

2. Background of Related Art

Circular stapling devices are utilized by clinicians to apply one or more surgical fasteners, e.g., staples or two-part fasteners, to body tissue for the purpose of joining segments of body tissue together and/or for the creation of an anastomosis. Circular stapling devices generally include a cartridge or shell assembly supporting a plurality of annular rows of staples, an anvil assembly operatively associated with the cartridge assembly and having annular arrays of staple receiving pockets for providing a surface against which the plurality of annular rows of staples can be formed, and an annular blade for cutting tissue.

During a typical tissue fastening procedure, the anvil assembly of the stapling device is positioned within one segment of body tissue and the shell assembly and a body portion of the stapling device supporting the shell assembly are positioned in an adjacent segment of body tissue. The anvil assembly is then attached to the body portion of the stapling device and the stapling device is actuated to approximate the anvil assembly with a staple cartridge of the shell assembly and clamp the body tissue segments together.

Typically, the anvil assembly includes an anvil shaft that includes splines that mate with splines formed within a shell housing of the shell assembly to align the staple forming pockets of the anvil assembly with staple receiving pockets of the staple cartridge of the shell assembly. The splines on the anvil shaft and on the shell housing of the shell assembly include left and right tapered ends that define an apex. When the right tapered ends of the splines of the anvil assembly engage the left tapered ends of the shell assembly (or vice versa), the anvil assembly will be rotated to allow the splines of the anvil assembly to pass between the splines of shell assembly to align the anvil assembly with the shell assembly. However, if the right tapered end of one spline of the anvil assembly engages the right tapered end of one spline of the shell assembly and a left tapered end of another spline of the anvil assembly engages the left tapered end of another spline of the shell assembly, or if the apexes of the splines of the anvil assembly and the shell assembly simultaneously hit head on, i.e., crash, the splines of the anvil assembly and the shell assembly may be damaged and/or the anvil assembly and the shell assembly may bind such that approximation of the anvil and shell assemblies is prevented or malformation of the staples may occur during firing of the stapling device.

A continuing need exist for a circular stapling device including more reliable alignment structure for aligning the staple forming pockets of the anvil assembly with the staple receiving pockets of the staple cartridge of the shell assembly.

SUMMARY

One aspect of the present disclosure is directed to an anvil assembly including an anvil shaft defining a longitudinal axis, and an anvil head assembly supported on a distal end of the anvil shaft including an anvil that defines a plurality of staple deforming recesses. The anvil shaft supports a plurality of splines including a first spline, a second spline and a third spline. Each of the first, second, and third splines includes a pair of tapered camming surfaces that meet at a proximal end of the respective spline to define an apex. The apex of the first spline is positioned on the anvil shaft at a location proximal of the apex of the second spline, and the apex of the second spline is positioned on the anvil shaft at a location proximal of the apex of the third spline.

Another aspect of the present disclosure is directed to a tool assembly including an anvil assembly and a shell assembly. The anvil assembly includes an anvil shaft defining a longitudinal axis and an anvil head assembly supported on a distal end portion of the anvil shaft. The anvil shaft supports a plurality of splines including a first spline, a second spline and a third spline. Each of the first, second, and third splines includes a pair of tapered camming surfaces that meet at a proximal end of each respective spline to define an apex. The apex of the first spline is positioned on the anvil shaft at a location proximal of the apex of the second spline, and the apex of the second spline is positioned on the anvil shaft at a location proximal of the apex of the third spline. The anvil head assembly supports an anvil that defines a plurality of staple deforming recesses. The shell assembly has a staple cartridge supporting a plurality of staples and a shell housing having an inner housing portion defining a plurality of housing splines. Adjacent splines of the plurality of housing splines define channels that are dimensioned to receive the first, second, and third splines of the anvil shaft.

In embodiments, the apex of the first spline is positioned on the anvil shaft proximally of the apex of the second spline a distance B, and the apex of the second spline is positioned on the anvil shaft proximally of the apex of the third spline a distance C, wherein B may be from about 0.15 mm to about 0.2 mm, and C may be from about 0.15 mm to about 0.2 mm.

In some embodiments, B and C are about 0.175 mm.

In certain embodiments, each of the first, second, and third splines defines a longitudinal axis that is parallel to the longitudinal axis of the anvil shaft, and the apex of the first spline is aligned with the longitudinal axis of the first spline.

In embodiments, the apex of the second spline is laterally offset from the longitudinal axis of the second spline a distance D and the apex of the third spline is laterally offset from the longitudinal axis of the third spline a distance E.

In some embodiments, the distance E is greater than the distance D.

In certain embodiments, D may be from about 0.15 mm to about 0.2 mm, and E may be from about 0.3 mm to about 0.4 mm.

Another aspect of the present disclosure is directed to an anvil assembly including an anvil shaft defining a longitudinal axis and an anvil head assembly supported on a distal end of the anvil shaft. The anvil shaft supports a plurality of splines including a first spline and a second spline. Each of the plurality of splines includes a pair of tapered camming surfaces that meet at a proximal end of the respective spline to define an apex. Each of the first and second splines defines a longitudinal axis that is parallel to the longitudinal axis of the anvil shaft. The apex of the first spline is aligned with the longitudinal axis of the first spline and the longitudinal axis of the second spline is laterally offset from the longitudinal axis of the second spline. The anvil head assembly supports an anvil that defines a plurality of staple deforming recesses.

In embodiments, the plurality of splines includes a third spline, wherein the apex of the second spline is laterally offset from the longitudinal axis of the second spline a distance D, and the apex of the third spline is laterally offset from the longitudinal axis of the third spline a distance E.

In some embodiments, E is greater than D.

In certain embodiments, the apex of the first spline is positioned proximally of apex of the second spline.

In embodiments, the apex of the first spline is positioned proximally of the second spline and the apex of the third spline is positioned proximally of the apex of the second spline.

BRIEF DESCRIPTION OF THE DRAWINGS

Various embodiments of the presently disclosed surgical stapling device are described hereinbelow with reference to the drawings, wherein:

FIG. 4 is a schematic view of a spline configuration of the anvil assembly of the "Prior Art" surgical stapling device shown in FIG. 3;

FIG. 5 is a side perspective view of the anvil assembly of the surgical stapling device shown in FIG. 1;

FIG. 5A is a cross-sectional view taken along section line 5A-5A of FIG. 5;

DETAILED DESCRIPTION OF EMBODIMENTS

Figure 1:
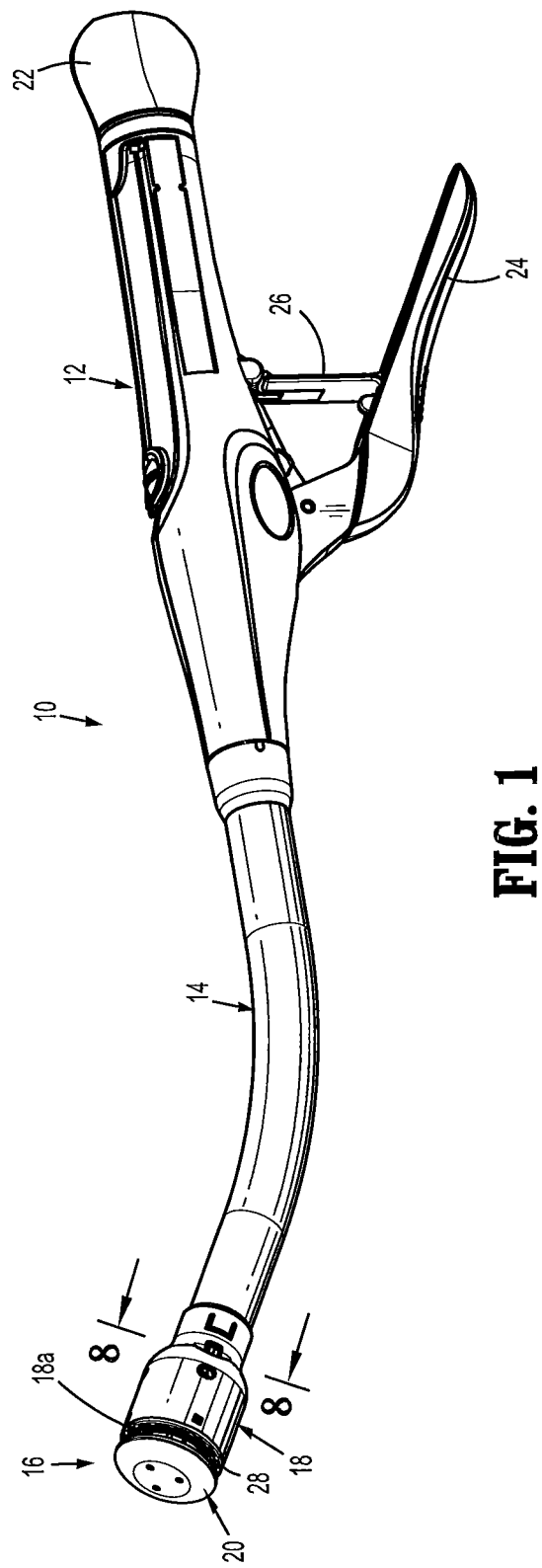
FIG. 1 is a side perspective view of an exemplary embodiment of the presently disclosed surgical stapling device with a tool assembly in a clamped position.

The presently disclosed surgical stapling device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term "endoscopic" is used generally to refer to endoscopic, laparoscopic, arthroscopic, and/or any other procedure conducted through small diameter incision or cannula, and the term "clinician" is used generally to refer to medical personnel including doctors, nurses, and support personnel. Further, as used herein the term "about" is used to mean plus or minus 10% of the identified parameter.

The presently disclosed surgical stapling devices include a tool assembly having an anvil assembly and a shell assembly. The anvil assembly includes an anvil shaft defining a longitudinal axis and an anvil head assembly supported on a distal end of the anvil shaft. The anvil shaft supports a plurality of splines including a first spline, a second spline and a third spline. Each of the first, second, and third splines includes a pair of tapered camming surfaces that meet at a proximal end of the respective spline to define an apex. The apex of the first spline is positioned on the anvil shaft at a location proximal of the apex of the second spline, and the apex of the second spline is positioned on the anvil shaft at a location proximal of the apex of the third spline. In embodiments, the apex of the first spline is aligned with a longitudinal axis of the first spline and the apex of the second and third splines are spaced laterally of a longitudinal axis of the second and third splines, respectively. The presently disclosed spline configuration reduces the likelihood that the splines of the anvil shaft will bind with splines of the shell assembly of the stapling device and that crashing of a spline of the anvil shaft with a spline of the shell assembly will significantly affect operation of the surgical stapling device.

Figure 2:
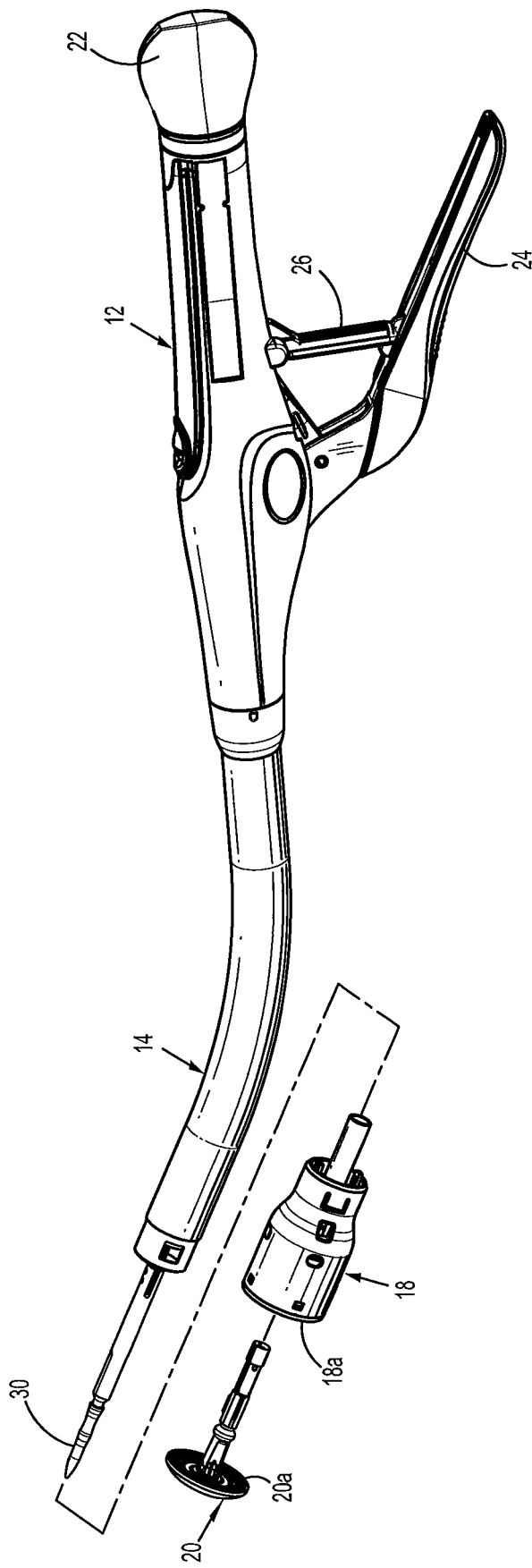
FIG. 2 is a side perspective view of the surgical stapling device shown in FIG. 1 with a shell assembly of the tool assembly and an anvil assembly of the tool assembly separated from the remaining portion of the stapling device.

Referring to FIGS. 1 and 2, the presently disclosed surgical stapling device shown generally as 10 includes a handle assembly 12, an elongated body portion 14 that extends distally from the handle assembly 12, and a tool assembly 16 that is supported on a distal portion of the elongated body portion 14. The tool assembly 16 includes a cartridge or shell assembly 18 that supports a staple cartridge 18a and an anvil assembly 20 that supports an anvil 20a. The handle assembly 12 includes an approximation knob 22 that operates an approximation mechanism (not shown) to move the anvil assembly 20 between unclamped and clamped positions in relation to the cartridge assembly 18, a firing trigger 24 that that operates a firing mechanism (not shown) to fire staples (not shown) from the staple cartridge 18a into tissue, and a firing trigger lockout 26 that is pivotally supported on the handle assembly 12 and is positioned to prevent inadvertent firing of the stapling device 10. For a detailed description of an exemplary circular stapling device including known approximation, firing, and lockout mechanisms, see U.S. Pat. No. 7,857,187 ("the '187 Patent") which is incorporated herein by reference in its entirety.

Although the presently disclosed stapling device 10 is shown and described as being a manually powered device, it is envisioned that the stapling device 10 can be an electrically powered device such as described in U.S. Patent Publication No. 2015/0048140 which is incorporated herein by reference in its entirety.

The staple cartridge 18*a* of the shell assembly 18 and the anvil 20*a* of the anvil assembly 20, have an annular configuration. The anvil assembly 20 is movable in relation to the shell assembly 18 from a spaced position to a clamped position to move the anvil 20*a* into juxtaposed alignment with the staple cartridge 18*a*. The staple cartridge 18*a* defines staple receiving slots 28 that are aligned with staple deforming recesses (not shown) of the anvil 20*a* when the staple cartridge 18*a* and the anvil 20*a* are properly aligned such that staples ejected from the staple receiving slots 28 are deformed within the staple receiving recesses when the stapling device 10 is fired.

The anvil assembly 20 is supported on an anvil retainer 30 (FIG. 2) which forms part of the approximation mechanism (not shown) of the stapling device 10. The anvil retainer 30 is configured to releasably engage the anvil assembly 20. The anvil retainer 30 includes a distal portion and a proximal portion. The distal portion of the anvil retainer 30 extends from a distal end of the elongate body portion 14 of the stapling device 10 and through the shell assembly 18 to a position to engage the anvil assembly 20. The proximal portion of the anvil retainer 30 is operatively connected to the approximation knob 22 such that rotation of the approximation knob 22 causes the anvil retainer 30 to move within the shell assembly 18 to move the anvil assembly 20 in relation to the staple cartridge 18*a* between the spaced position and the clamped position. The shell assembly 18 includes an annular knife (not shown) that is movable from a retracted position to an advanced position within the shell assembly 18 during firing of the stapling device 10 to transect tissue clamped between the staple cartridge 18*a* and the anvil 20*a*.

Referring to FIG. 2, the shell assembly 18 is releasably coupled to a distal portion of the elongated body 14 of the stapling device 10 to facilitate replacement of the shell assembly 18 after each firing of the stapling device 10. Mechanisms for releasably coupling the shell assembly 18 to the elongate body portion 14 of the stapling device 10 are described in U.S. Patent Publication Nos. 2016/0310141, 2016/0192938, and 2016/0192934 which are incorporated herein in their entirety by reference.

Figure 3:
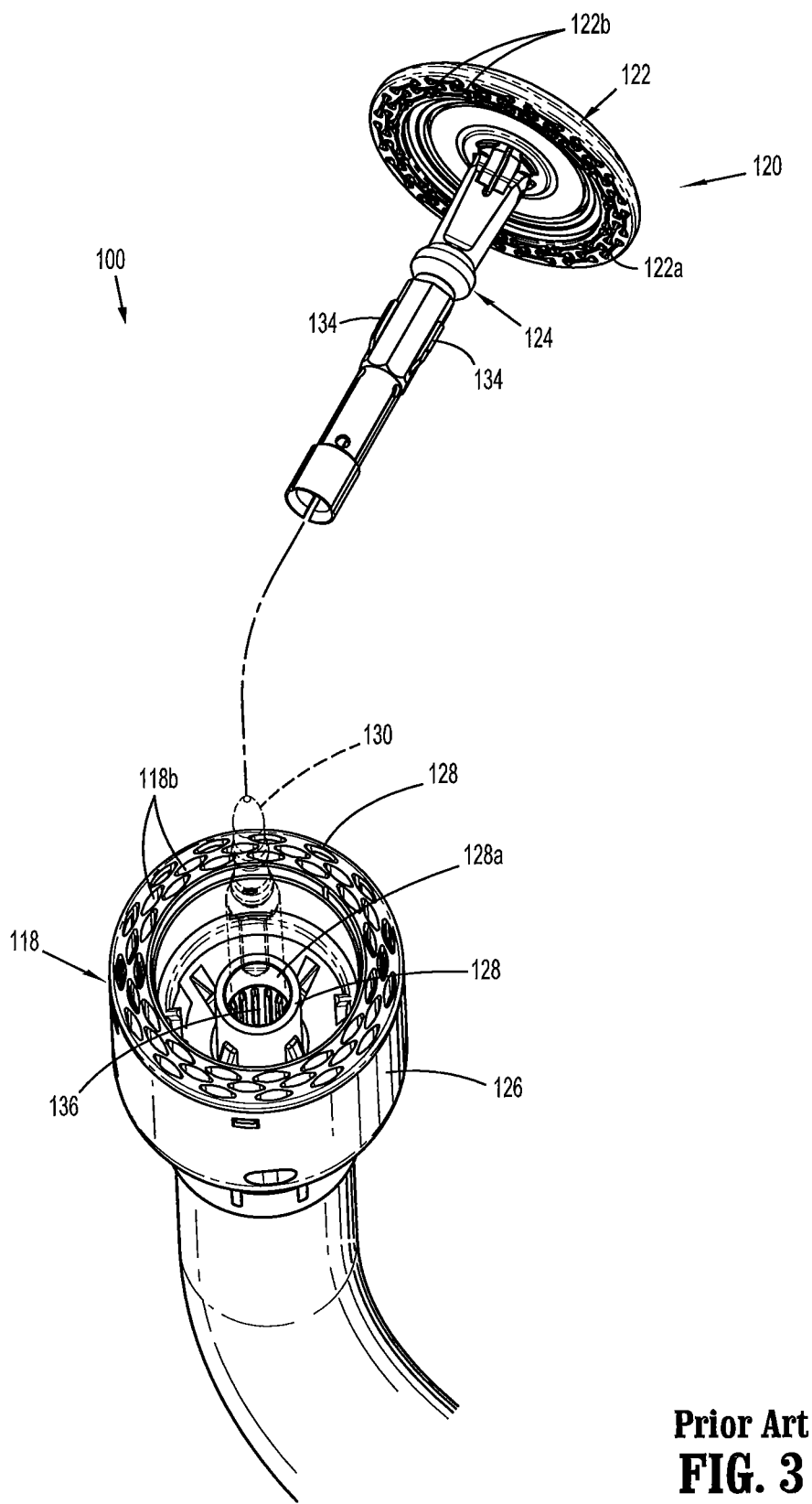
FIG. 3 is a perspective view from a distal end of a "Prior Art" surgical stapling device with the anvil assembly of the tool assembly of the surgical stapling device separated from an anvil retainer (shown in phantom) of the surgical stapling device.

Referring to FIG. 3, in "Prior Art" circular stapling devices 100, an anvil assembly 120 includes an anvil head 122 and an anvil shaft 124, and a shell assembly 118 includes a staple cartridge 118*a* and a shell housing 126 having an inner housing portion 128 that defines a through bore 128*a*. The anvil head 122 supports an anvil 122*a* that defines annular arrays of staple deforming recesses 122*b* and the staple cartridge 118*a* defines annular arrays of staple receiving slots 118*b*. An anvil retainer 130 (shown in phantom) includes a distal end that is configured to releasably engage the anvil shaft 124 of the anvil assembly 120. The anvil retainer 130 is received within the through bore 128*a* and is movable between retracted and advanced positions. When the anvil shaft 124 is coupled to the anvil retainer 130 and the anvil retainer 130 is retracted (via actuation of the approximation knob 22, FIG. 1), the anvil shaft 124 is drawn into the through bore 128*a* of the inner housing portion 128 of the shell housing 126.

In order to align the arrays of staple deforming recesses 122*b* of the anvil head 122 of the anvil assembly 120 with the staple receiving slots 118*b* of the staple cartridge 118*a* of the shell assembly 118, the anvil shaft 124 includes a plurality of splines 134 including adjacent splines 134*a*, 134*b* (FIG. 4) that are received between splines 136 formed along an inner wall of the inner housing portion 128 of the shell housing 126. Each of the splines 134 of the anvil assembly 120 defines a central axis "Z" and left and right tapered cam surfaces 138*a*, 138*b* positioned on opposite sides of the central axis "Z" as viewed in FIG. 4. The tapered surfaces 138*a*, 138*b* meet at their proximal ends at an apex 140. Similarly, each of the splines 136 of the shell assembly 118 defines a central axis "X" and left and right tapered cam surfaces 142*a*, 142*b* positioned on opposite sides of the central axis "X". The tapered surfaces 142*a*, 142*b* meet at their distal ends at an apex 144.

When the anvil assembly 120 is attached to the anvil retainer 130 and the anvil retainer 130 and anvil assembly 120 are retracted into the through bore 128*a* (FIG. 3) of the inner housing portion 128 of the shell housing 126, the splines 134 of the anvil assembly 120 move towards the splines 136 of the shell assembly 118. If the splines 134 are misaligned with channels 148 defined between the splines 136 of the shell assembly 118, the apexes 140 of the anvil splines 134*a*, 134*b* will engage one of the cam surfaces 142*a*, 142*b* of the splines 136. When all of the apexes 140 of all of the splines 134*a*, 134*b* (only two are shown) engage the left tapered cam surface 142*a* of the splines 136, the engagement urges or cams the anvil assembly 120 to rotate in the direction indicated by arrow "S" to realign the splines 134*a*, 134*b* so that they enter into the channels 148 defined between the splines 136 of the shell assembly 118. Similarly, when all of the apexes 140 of all of the splines 134*a*, 134*b* engage the right tapered cam surface 142*b* of the splines 136, the engagement urges or cams the anvil assembly 120 to rotate in the direction indicated by arrow "T" to realign the splines 134*a*, 134*b* so that they enter into the channels 148 defined between the splines 136 of the shell assembly 118. However, if the apexes 140 of any two of the splines 134*a*, 134*b* simultaneously engage the left and right tapered cam surfaces 142*a*, 142*b* of the two splines 136 of the shell assembly 118, the engagement simultaneously urges or cams the anvil assembly 120 in opposite directions. When this happens, the splines 134*a-b* and 136 will bind until one or both of the splines 134 and/or 136 fractures. In addition, if the apexes 140 of the splines 134*a-b* are aligned with the apexes 144 of the splines 136, the apexes may crash into each other causing damage to the splines 134*a-b* and/or 136. When the splines 134 and 136 crash into or bind with each other and proper alignment between staple receiving recesses 127 of the anvil assembly 120 and staple receiving slots 128 of the shell assembly 118 is not achieved, improper staple formation or locking of the stapling device 100 may result.

Figure 6:
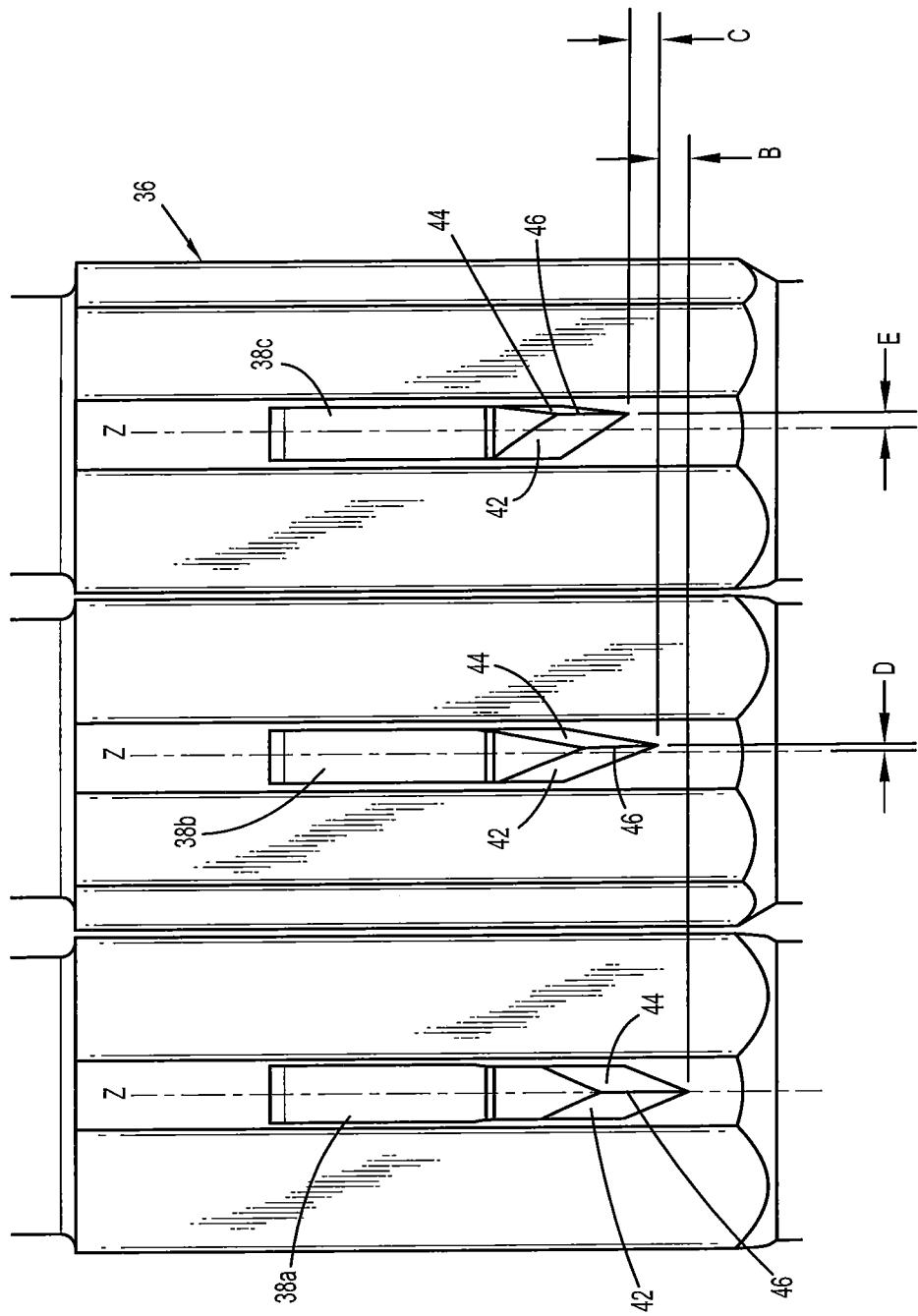
FIG. 6 is a side view taken in the direction indicated by arrows 6-6 of FIG. 5.

Referring to FIGS. 5 and 6, in the presently disclosed surgical stapling device 10 (FIG. 1), the anvil assembly 20 includes an anvil head assembly 34 which supports the anvil 20*a* and an anvil shaft 36 defining a longitudinal axis "SH" (FIG. 5). The anvil shaft 36 supports a plurality of splines 38 positioned about the anvil shaft 36 including a first spline 38*a*, a second spline 38*b*, and a third spline 38*c*. In some embodiments, the plurality of splines 38 includes first and second splines 38*a*, 38*b*. Each of the splines 38*a-c* defines a longitudinal axis "Z" (FIG. 6) that extends in a direction that is substantially parallel to the longitudinal axis "SH" (FIG. 5) of the anvil shaft 36 and includes left and right tapered cam surfaces 42 and 44 (as viewed in FIG. 6), respectively, that meet to define an apex 46 positioned at a proximal end of the respective spline 38. In embodiments, the apex 46 of the spline 38*a* is positioned proximally of the apex 46 of the spline 38b by a distance of "B" (FIG. 6) where "B" may be from about 0.15 mm to about 0.2 mm, and the apex 46 of the spline 36b is positioned proximally of the apex 38c by a distance of "C", where "C" may be from about 0.15 mm to about 0.2 mm. By spacing the apexes 46 of the splines 36 along the longitudinal axis "SH" of the anvil shaft 36, the likelihood that two or more of the apexes 46 of the splines 38 will simultaneously engage of apexes of the splines 54 (FIG. 7A) of the shell assembly 18 or that the apexes 46 of the splines 38 of the anvil assembly 20 will simultaneously engage opposite sides of respective splines 54 of the shell assembly 18 to cause crashing or binding of the splines is minimized.

Referring to FIG. 6, in embodiments, the apex 46 of the first spline 38a is aligned with the longitudinal axis "Z" of the first spline 38a and includes left and right tapered cam surfaces 42, 44 of substantially equal size. In contrast, the apex 46 of the second spline 38b is offset from the longitudinal axis "Z" by a distance "D", and the apex 46 of the third spline 38c is offset from the longitudinal axis "Z" by a distance of "E", wherein the distance "D" may be from about 0.15 mm to about 0.2 mm, and the distance "E" may be from about 0.3 mm to about 0.4 mm. As such, the size of the left cam surfaces 42 of the splines 38b-c, are larger than the size of the right cam surfaces 44 of the splines 38b-c.

Figure 7A:
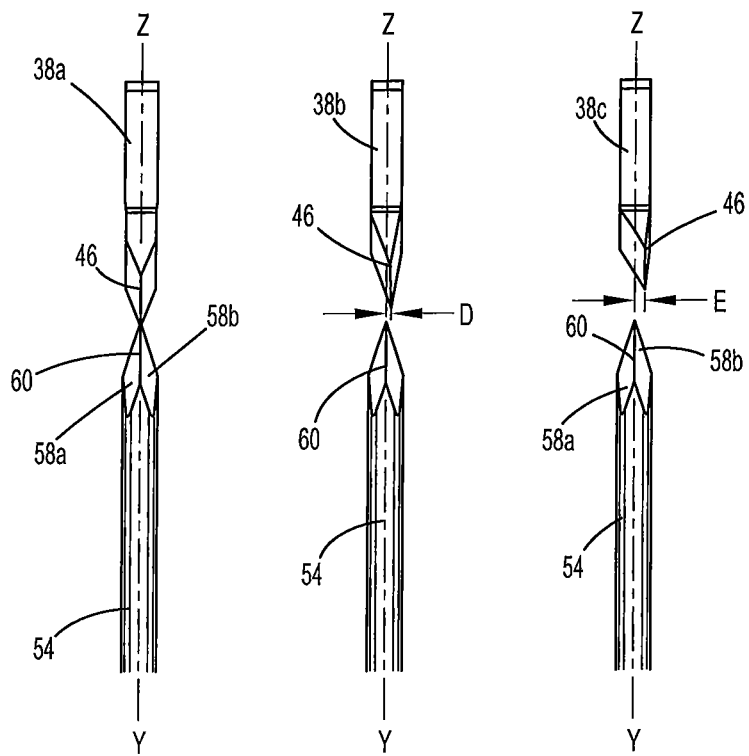
FIG. 7A is a schematic view of the spline configuration of the anvil assembly shown in FIG. 6 as a first spline of a plurality of splines on the anvil assembly engages a first spline of a plurality of splines of the shell assembly.
Figure 7B:
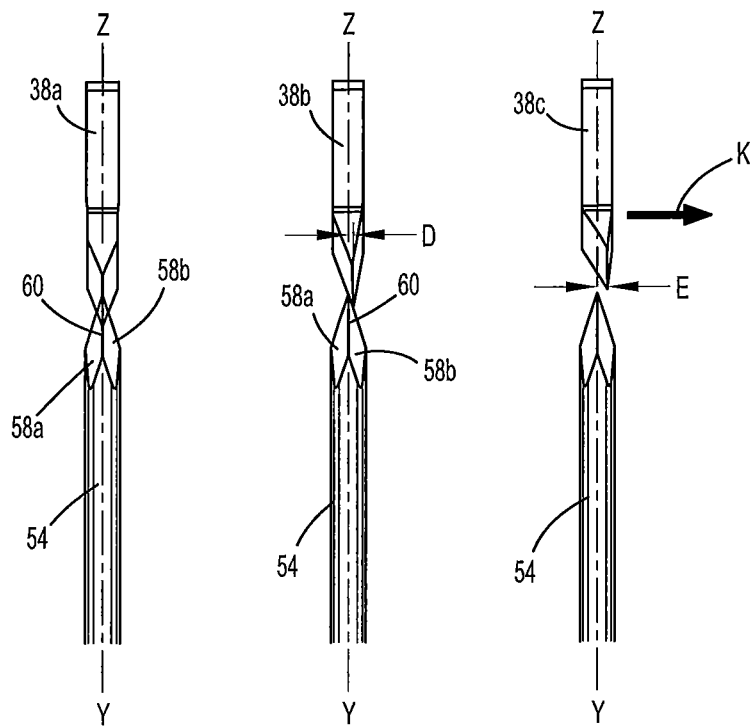
FIG. 7B is a schematic view of the spline configuration of the anvil assembly shown in FIG. 6 as a second spline of the plurality of splines on the anvil assembly engages the second spline of the plurality of splines of the shell assembly.
Figure 7C:
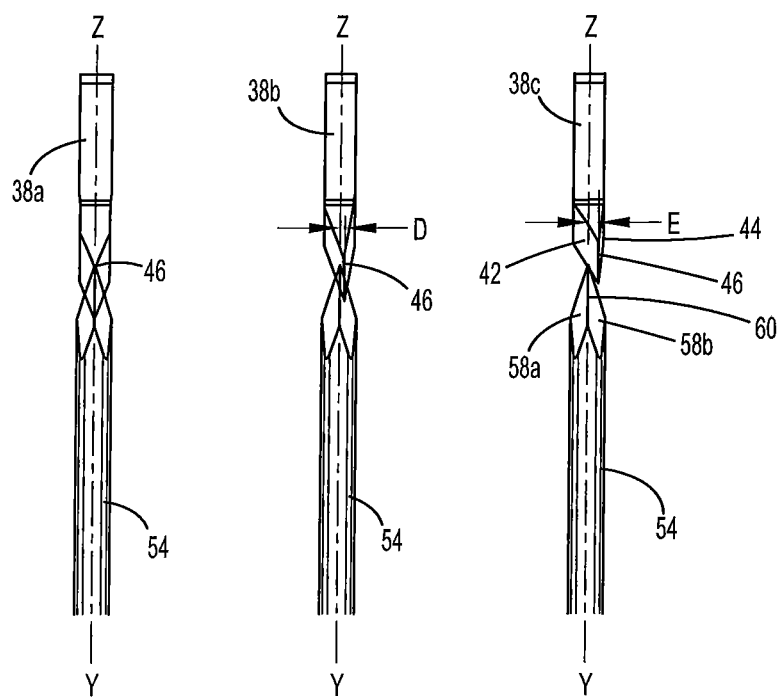
FIG. 7C is a schematic view of the spline configuration of the anvil assembly shown in FIG. 6 as a third spline of the plurality of splines on the anvil assembly engages a third spline of the plurality of splines of the shell assembly.
Figure 8:
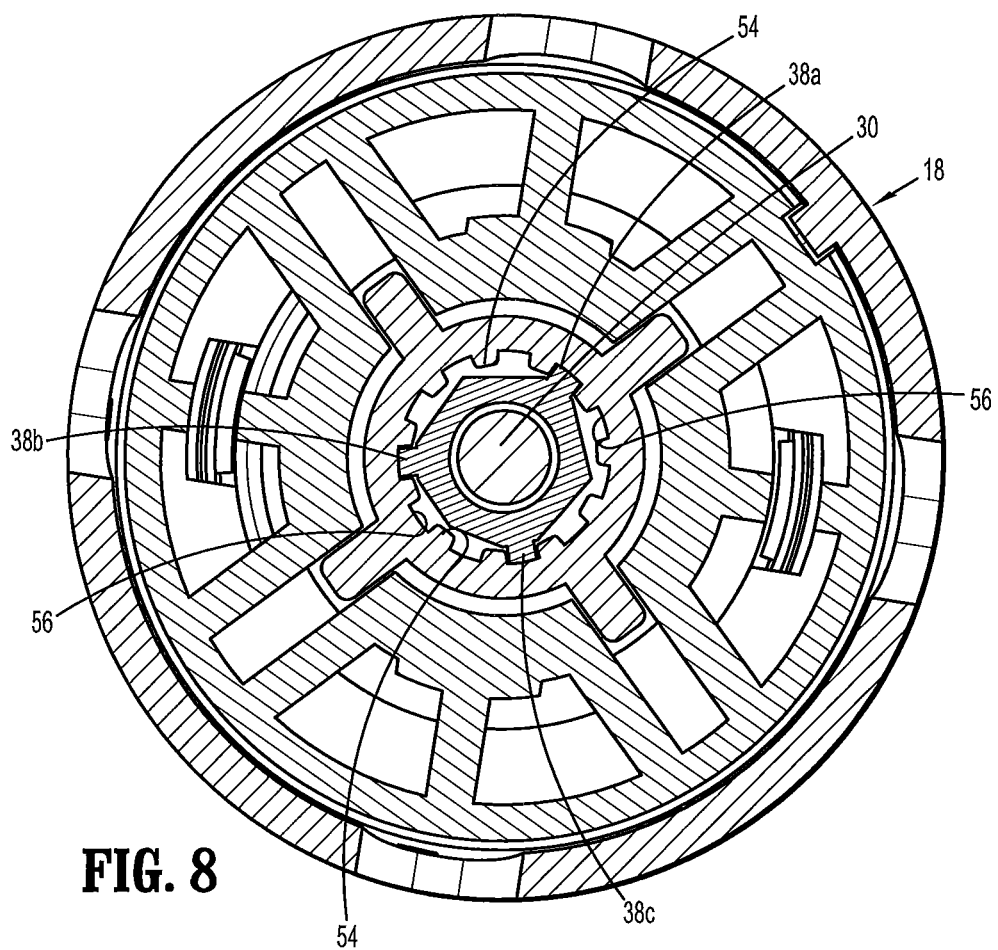
FIG. 8 is a cross-sectional view taken along section line 8-8 of FIG. 1.

Referring to FIGS. 7A-8, as discussed above in regard to the "Prior Art" stapling device shown in FIGS. 3 and 4, the shell assembly 18 (FIG. 2) of the stapling device 10 (FIG. 1) includes a plurality of spaced splines 54, each defining a central longitudinal axis "Y" (FIGS. 7A-7C). Adjacent splines 54 of the plurality of splines 54 define channels 56 (FIG. 8) between each of the splines 54. Each of the splines 54 includes left and right tapered cam surfaces 58a, 58b (as viewed in FIGS. 7A-7C) that are positioned on opposite sides of the central longitudinal axis "Y" of the spline 54. The tapered surfaces 58a, 58b meet at their distal ends at an apex 60.

When the anvil assembly 20 is approximated towards the shell assembly 18 of the stapling device 10 towards the clamped position (FIG. 1), the splines 38a-c of the anvil assembly 20 approach the splines 54 of the shell assembly 18. Initially, the apex 46 of the first spline 38a contacts one of the plurality of splines 54 (FIG. 7A). As discussed above, the apex 46 of the spline 38a is positioned proximally of the apexes 46 of the splines 38b-c such that only the apex 46 of the spline 38a initially will engage the splines 54 of the shell assembly 18. In circumstances in which the axis "Z" of the spline 38a is aligned with the axis "Y" of the spline 54 (as shown in FIG. 7A) crashing of the splines 38a and 54 may occur. Since only the apex 46 of the first spline 38a initially contacts the apex 60 of one of a respective spline 54 (FIG. 7A) of the shell assembly 18, crashing is limited to only that one spline 38a.

If the engagement of the spline 38a and the spline 54 does not cause the anvil assembly 20 to be cammed or to rotate into alignment with the shell assembly 18, continued approximation of the anvil assembly 20 in relation to the shell assembly 18 causes the apex 46 of the second spline 38b of the anvil assembly 20 to engage another spline 54 of the shell assembly 18 (FIG. 7B). As discussed above, the apex 46 of the second spline 38b is offset from the longitudinal axis "Z" of the spline 38b. As such, when apex 46 of the spline 38b of the anvil assembly 20 engages the spline 54 of the shell assembly 18, the apex 46 of the spline 38b is positioned offset from the apex 60 of the spline 54. Thus, the apex 46 of the spline 38b will engage one of the left or right tapered cam surfaces 58a, 58b of the spline 38c (right tapered cam surface 58b as shown in FIG. 7B such that the anvil assembly 20 is cammed or rotated in the direction indicated by arrow "K" in FIG. 7B. As the anvil assembly 20 is rotated in the direction indicated by arrow "K", the splines 38a-c are rotated towards a position aligned with the channels 56 (FIG. 8) of the shell assembly 18. When this occurs, the apex 46 of the spline 38a of the anvil shaft 36 will rotate out of engagement with the apex 60 of the spline 54 of the shell assembly 18.

As the anvil assembly 20 continues to be advanced in relation to the shell assembly 18 toward a clamped position, the third spline 38c of the anvil assembly 20 (FIG. 1) engages another spline 54 of the shell assembly 18. As discussed above, the apex 46 of the spline 38c is further offset from the longitudinal axis "Z" of the spline 38c. As the anvil assembly 20 continues to be advanced in relation to the shell assembly 18, the apex 46 of the spline 38c of the anvil shaft 36 engages one of the left and right tapered cam surfaces 58a, 58b of the spline 54 of the shell assembly 18 (right tapered cam surface 58b as shown in FIG. 7C). Engagement of the spline 38c of the anvil assembly 20 with the spline 54 of the shell assembly 18 further assists in camming the anvil assembly 20 to a position in which the splines 38a-c are aligned with the channels 56 (FIG. 8) of the shell assembly 18.

In embodiments, the presently disclosed anvil assembly 20 (FIG. 1) includes a plurality of splines 38a-c that are positioned on the anvil shaft 36 (FIG. 5) and have proximal ends that are longitudinally offset from each other. By longitudinally spacing the proximal ends of the splines 38a-c along the anvil shaft 36 of the anvil assembly 20, any likelihood that any two splines of the plurality splines 38a-c will simultaneously engage opposite sides of respective splines 54 of a shell assembly 18 is substantially decreased. This substantially decreases any likelihood that the splines 38a-c of the anvil assembly 20 will bind with the splines 54 of the shell assembly 18. In addition, laterally offsetting the apex of the splines 38b-c of the anvil assembly 20 from the longitudinal axis "Z" of the splines 38b-c allows the anvil assembly 20 to be rotated from a position in which the apexes of the splines 38a-c are aligned with the apexes 60 of the splines 54 of the shell assembly 18 wherein the proximal-most spline 38a crashes into a respective spline 54 of the shell assembly 18.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil assembly comprising:
an anvil shaft defining a longitudinal axis, the anvil shaft supporting a first spline, a second spline and a third spline, each of the first, second, and third splines including a pair of tapered camming surfaces that meet at a proximal end of the respective spline to define an apex, the apex of the first spline being positioned on the anvil shaft at a location proximal of the apex of the second spline, and the apex of the second spline being positioned on the anvil shaft at a location proximal of the apex of the third spline; and an anvil head assembly supported on a distal end portion of the anvil shaft, the anvil head assembly supporting an anvil that defines a plurality of staple deforming recesses.

2. The anvil assembly of claim 1, wherein the apex of the first spline is positioned on the anvil shaft proximally of the apex of the second spline a distance B, and the apex of the second spline is positioned on the anvil shaft proximally of the apex of the third spline a distance C, wherein B is from about 0.15 mm to about 0.2 mm, and C is from about 0.15 mm to about 0.2 mm.

3. The anvil assembly of claim 2, wherein B is about 0.175 mm.

4. The anvil assembly of claim 1, wherein each of the first, second, and third splines defines a longitudinal axis that is parallel to the longitudinal axis of the anvil shaft, wherein the apex of the first spline is aligned with the longitudinal axis of the first spline.

5. The anvil assembly of claim 4, wherein the apex of the second spline is laterally offset from the longitudinal axis of the second spline a distance D and the apex of the third spline is laterally offset from the longitudinal axis of the third spline a distance E.

6. The anvil assembly of claim 5, wherein the distance E is greater than the distance D.

7. The anvil assembly of claim 6, wherein D is from about 0.15 mm to about 0.2 mm, and E is from about 0.3 mm to about 0.4 mm.

8. A tool assembly comprising:
an anvil assembly including:
an anvil shaft defining a longitudinal axis, the anvil shaft supporting a first spline, a second spline and a third spline, each of the first, second, and third splines including a pair of tapered camming surfaces that meet at a proximal end of the respective spline to define an apex, the apex of the first spline being positioned on the anvil shaft at a location proximal of the apex of the second spline, and the apex of the second spline being positioned on the anvil shaft at a location proximal of the apex of the third spline; and
an anvil head assembly supported on a distal end portion of the anvil shaft, the anvil head assembly supporting an anvil that defines a plurality of staple deforming recesses; and
a shell assembly having a staple cartridge supporting a plurality of staples, and a shell housing having an inner housing portion defining a plurality of housing splines, wherein adjacent splines of the plurality of housing splines define channels, the channels being dimensioned to receive the first, second, and third splines of the anvil shaft.

9. The tool assembly of claim 8, wherein the apex of the first spline of the anvil shaft is positioned proximally of the apex of the second spline of the anvil shaft a distance B, and the apex of the second spline of the anvil shaft is positioned proximally of the apex of the third spline a distance C, wherein B is from about 0.15 mm to about 0.2 mm, and C is from about 0.15 mm to about 0.2 mm.

10. The tool assembly of claim 9, wherein B and C are about 0.175 mm.

11. The tool assembly of claim 8, wherein each of the first, second, and third splines defines a longitudinal axis that is parallel to the longitudinal axis of the anvil shaft, wherein the apex of the first spline is aligned with the longitudinal axis of the first spline.

12. The tool assembly of claim 11, wherein the apex of the second spline is laterally offset from the longitudinal axis of the second spline a distance D and the apex of the third spline is laterally offset from the longitudinal axis of the third spline a distance E.

13. The tool assembly of claim 12, wherein the distance E is greater than the distance D.

14. The tool assembly of claim 13, wherein the distance D is from about 0.15 mm to about 0.2 mm, and the distance E is from about 0.3 mm to about 0.4.

15. An anvil assembly comprising:
an anvil shaft defining a longitudinal axis, the anvil shaft supporting a plurality of splines including a first spline and a second spline, each of the plurality of splines including a pair of tapered camming surfaces that meet at a proximal end of the respective spline to define an apex, wherein each of the first and second splines defines a longitudinal axis that is parallel to the longitudinal axis of the anvil shaft, the apex of the first spline being aligned with the longitudinal axis of the first spline and the apex of the second spline being laterally offset from the longitudinal axis of the second spline; and
an anvil head assembly supported on a distal end portion of the anvil shaft, the anvil head assembly supporting an anvil that defines a plurality of staple deforming recesses.

16. The anvil assembly of claim 15, wherein the plurality of splines includes a third spline, the apex of the second spline being laterally offset from the longitudinal axis of the second spline a distance D and the apex of the third spline being laterally offset from the longitudinal axis of the third spline a distance E.

17. The anvil assembly of claim 16, wherein E is greater than D.

18. The anvil assembly of claim 17, wherein the apex of the first spline is positioned proximally of the second spline and the apex of the second spline is positioned proximally of the apex of the third spline.

19. The anvil assembly of claim 15, wherein the apex of the first spline is positioned proximally of apex of the second spline.

* * * * *